United States Patent [19]

Lewin et al.

[11] 4,386,405

[45] May 31, 1983

[54] DEVICE FOR MEASURING THE LOCATION, THE ATTITUDE AND/OR A CHANGE OF LOCATION OR ATTITUDE OF THE LOWER JAW OF A PATIENT

[75] Inventors: Arthur Lewin, Saxonwold, South Africa; Bernd Nickel, Lorsch, Fed. Rep. of Germany

[73] Assignee: Siemens Aktiengesellschaft, Berlin & Munich, Fed. Rep. of Germany

[21] Appl. No.: 203,144

[22] Filed: Nov. 3, 1980

[30] Foreign Application Priority Data

Nov. 3, 1979 [DE] Fed. Rep. of Germany ....... 2944489

[51] Int. Cl.³ .......................... G06G 7/60; A61B 5/05
[52] U.S. Cl. .................................... 364/415; 128/777; 433/69
[58] Field of Search ........................ 364/415, 815–818; 433/68, 69; 128/653, 777, 774, 782, 776, 1.3

[56] References Cited

U.S. PATENT DOCUMENTS

| | | | |
|---|---|---|---|
| 3,390,459 | 7/1968 | Seidenberg | 433/69 X |
| 3,822,694 | 7/1974 | Mills | 128/653 X |
| 3,883,954 | 5/1975 | Simmering et al. | 433/68 X |
| 4,197,855 | 4/1980 | Lewin | 128/777 X |
| 4,303,077 | 12/1981 | Lewin et al. | 128/777 |
| 4,303,919 | 12/1981 | Dimeff | 433/68 X |

OTHER PUBLICATIONS

McCutcheon et al., "Video Scanning System for Measurement of Lip and Jaw Motion, " J. Acoust. Soc. Am., vol. 61, No. 4 (Apr. 1977) pp. 1051-1055.

Primary Examiner—Joseph F. Ruggiero
Attorney, Agent, or Firm—Hill, Van Santen, Steadman, Chiara & Simpson

[57] ABSTRACT

The illustrated embodiment employs a field generator, preferably a magnetic field generator, field flux pickups arranged at an interval therefrom, as well as an electronic device for the three-dimensional comprehension and evaluation of electrical signals arising in a field flux or a change of field flux. For displaying random points ($P_2 ... P_n$) of the lower jaw (1), means are provided which identify the geometrical attitude of the points with respect to a fixed-body coordinate system ($x_o$, $y_o$, $Z_o$) allocated to the lower jaw whose origin and rotational center is the measuring point ($P_1$). Further, a coordinate converter is provided which converts the coordinates ($x_o$, $y_o$, $z_o$) related to the lower jaw into the coordinates ($\Delta x_2$, $\Delta y_{22}$ $\Delta z_2$) of the stationary coordinate system (X, Y, Z). Further, summing amplifiers are provided which add the adjustment magnitudes ($\Delta x_2$, $\Delta y_2$, $\Delta z_2$) of the jaw-related coordinates to the coordinates ($x_1$, $y_1$, $z_1$) of the measuring point ($P_1$). The device is particularly employed in gnathography.

12 Claims, 6 Drawing Figures

DEVICE FOR MEASURING THE LOCATION, THE ATTITUDE AND/OR A CHANGE OF LOCATION OR ATTITUDE OF THE LOWER JAW OF A PATIENT

BACKGROUND OF THE INVENTION

The invention relates to a device for the measurement of the location, of the attitude and/or of a change of location or attitude of the lower jaw of a patient upon employment of a field generator, preferably a magnetic field generator, field flux pick-ups arranged at an interval therefrom, as well as an electronic device for the three-dimensional comprehension and evaluation of electrical signals arising in a field flux or, respectively, in a change of field flux.

Such a device is described in the German Pat. application No. P 28 14 551.9 (and in the corresponding U.S. application Ser. No. 025,263 filed Mar. 29, 1979), now U.S. Pat. No. 4,303,077 issued Dec. 1, 1981. The signals gained with the device revealed there, however, only cover one point of the lower jaw, namely the measuring point at which the field generator is secured. The signals ($x_1$, $y_1$, $z_1$) gained therefrom thus correspond to the coordinates of this one point on the lower jaw. In addition, information concerning a rotational movement ($\alpha$, $\beta$, $\gamma$) around the coordinate axes X, Y, Z are gained with this device.

The representation of a point of the lower jaw does not produce a statement concerning the attitude and the course of movement of the entire lower jaw.

SUMMARY OF THE INVENTION

The object of the invention is to specify an improved device, particularly with the goal of being able to cover and record not only one point but, rather, as many points of the lower jaw as desired with respect to the attitude, to the location and to the course of the motion.

This object is inventively achieved in that means for covering the geometrical attitude of random points of the lower jaw with respect to a body-fixed coordinate system allocated to the lower jaw whose origin and center of rotation is the measuring point, are provided; in that a coordinate converter is present which transforms the coordinates related to the lower jaw into the coordinates of the fixed coordinate system; and in that summing amplifiers are present which add the adjustment magnitudes of the jaw-related coordinates to the coordinates of the measuring point.

Advantageous embodiments and further developments of the invention are defined in the subclaims. In the following, an exemplary embodiment of the invention is described in greater detail on the basis of the accompanying drawing sheets; and other objects, features and advantages will be apparent from this detailed disclosure and from the appended claims.

DETAILED DESCRIPTION

Figure 1:
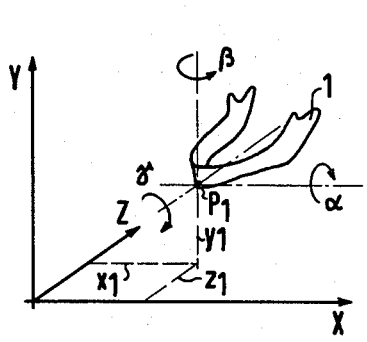
FIG. 1 is a perspective view of a lower jaw in a coordinate system.
Figure 2:
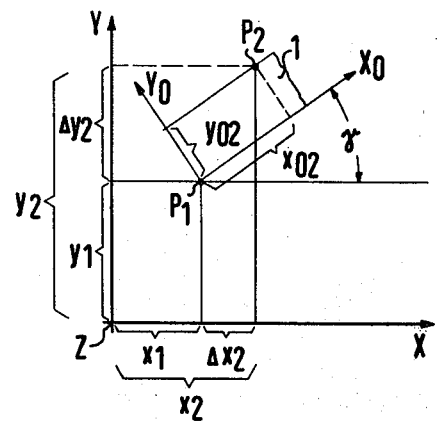
FIG. 2 is a basic illustration for the explanation of the coordinate relationships.

The relation of the measuring point to which the field generator (magnetic field generator) is secured to the flux pick-ups is explained on the basis of FIG. 1. The measuring point at which the field generator is situated is referenced with $P_1$. The measuring point $P_1$ is fixed by the disposition of the field generator and moves together with the lower jaw referenced with 1. In the course of further consideration, $P_1$ is viewed as being in the rotational center of the rotations $\alpha$, $\beta$, $\gamma$. The coordinates of the measuring point $P_1$ from the coordinate zero point are referenced with $x_1$, $y_1$ and $z_1$. The coordinate values $x_1$, $y_1$, $z_1$ as well as the rotational information from $\alpha$, $\beta$, $\gamma$ are supplied from the means described in the aforementioned patent application. FIG. 2 reproduces the coordinate relationships schematically for the X-Y plane. The Z-axis is perpendicular to the plane of the drawing.

$P_2$ indicates a randomly selectable point on the lower jaw 1 which is to be visually displayed together with further points ($P_3 \ldots P_n$). It is assumed in the illustration that the lower jaw 1 is rotated by the angle $\gamma$ around an axis proceeding through $P_1$ and which is parallel to the Z-axis. A fixed-body coordinate system $X_o$, $Y_o$ and $Z_o$ is assigned to the lower jaw 1; with respect to this (jaw-related) coordinate system, the point $P_2$ has the coordinates $x_{o2}$, $y_{o2}$. Excluding a rotation around the angle $\gamma$, the point $P_2$ has the coordinates $x_1 + x_{o2}$ and $y_1 + y_{o2}$ with respect to the coordinate system X, Y. Given the rotation around the angle $\gamma$ illustrated in FIG. 2, the adjustment magnitudes $\Delta x$ and $\Delta y$ derive for the point $P_2$ with respect to the stationary coordinate system X, Y. The analogous case applies to the Z axis. The fixed-body coordinate system $X_o$, $Y_o$ (and, under certain conditions $Z_o$) serves, together with the angle $\gamma$, to determine the relative attitude of the point $P_2$ with respect to $P_1$ in the stationary coordinate system X, Y. In the arrangement illustrated in FIG. 2, a rotational movement of the lower jaw 1 ensues through the point $P_1$ around an axis parallel to the Z axis. In order to determine the new coordinates, the adjustment magnitudes $\Delta x_2$, $\Delta y_2$, $\Delta z_2$ are to be employed for this purpose. These adjustment magnitudes are calculated together with the measured values $x_1$, $y_1$ and $z_1$ according to the equation:

$$x_2 = x_{o2} \cdot \cos \gamma - y_{o2} \cdot \sin \gamma$$

$$y_2 = x_{o2} \cdot \sin \gamma + y_{o2} \cdot \cos \gamma$$

Figure 4:
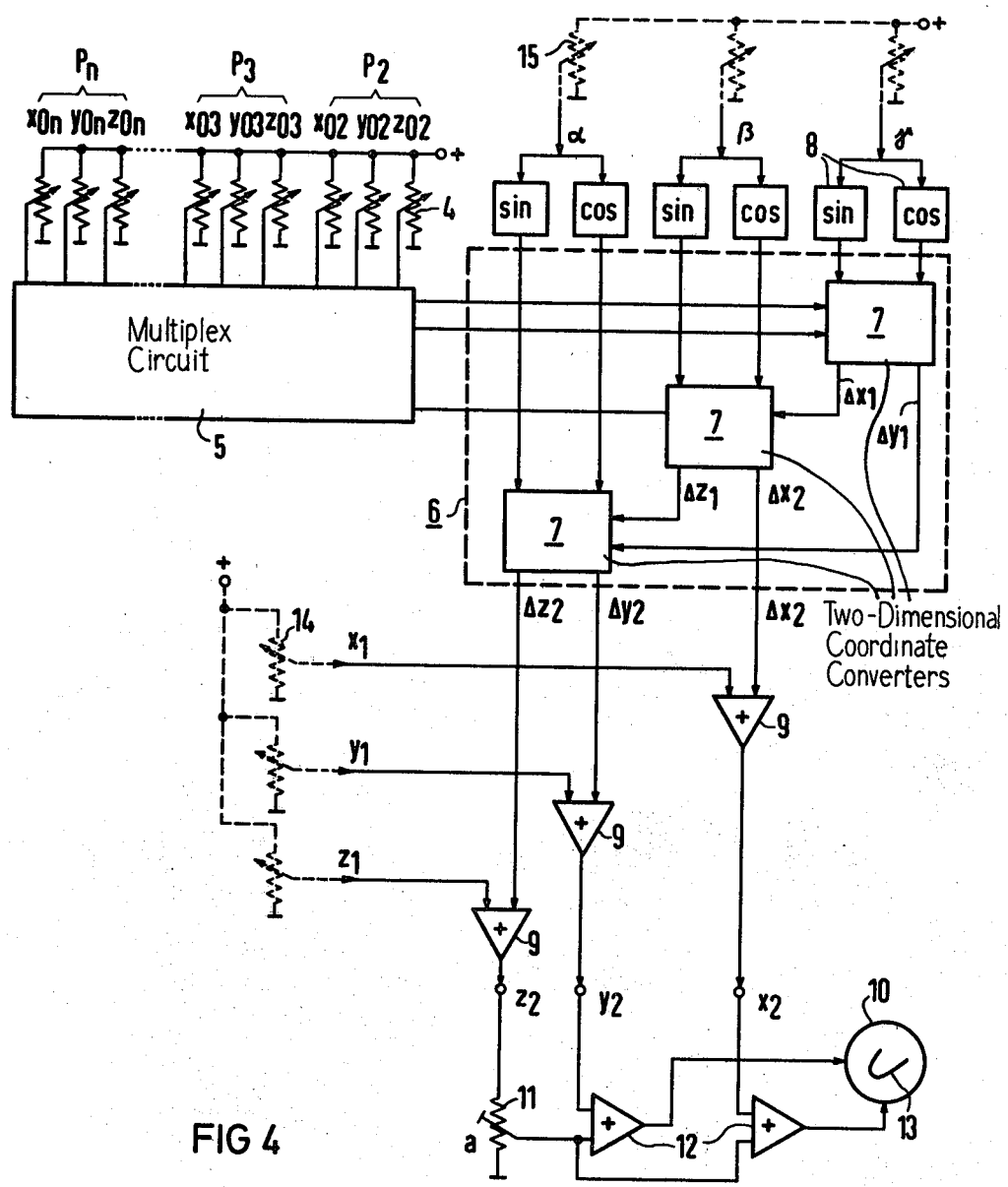
FIG. 4 is a block diagram of a system for calculating and evaluating the coordinates.

An evaluation in accord with the block diagram of FIG. 4 ensues for $\Delta z_2$.

For the point $P_2$, the following derives with respect to the stationary coordinate system X, Y, Z:

$$x_2 = x_1 + \Delta x = x_1 + x_{o2} \cdot \cos \gamma - y_{o2} \cdot \sin \gamma$$

$$y_2 = y_1 + \Delta y = y_1 + x_{o2} \cdot \sin \gamma + y_{o2} \cdot \cos \gamma.$$

Figure 3:
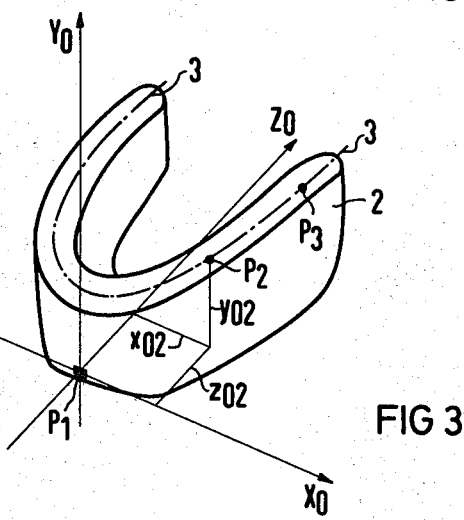
FIG. 3 shows a jaw impression model in a schematic presentation.

FIG. 3 shows a jaw impression model 2 with the measuring point $P_1$ in which the magnetic field generator is situated in a schematic illustration. Let it be assumed that the points $P_2$, $P_3 \ldots P_n$ to be imaged are to be situated on a center line referenced with 3. The point $P_2$ has the coordinate values $x_{o2}$, $y_{o2}$, $z_{o2}$. These coordinates are picked up e.g. automatically by means of suitable measuring devices, and such devices may effect the automatic setting of memory devices 4, FIG. 4. (Such automatic measurement devices per se are well known in the art.)

Instead of an impression model, an x-ray film image can also be employed which, depending upon the points to be presented, can be a front, side, or top view of the jaw. The points to be imaged can be picked up either with the assistance of suitable matrix devices (millimeter paper) or with the assistance of automatic opto-electronic scanning devices.

The signal evaluation is explained in greater detail on the basis of FIG. 4. Coordinate values for the points $P_2$, $P_3 \ldots P_n$ to be imaged are input into the analog memory 4 according to the measured values $x_{o2}$, $y_{o2}$, $z_{o2} \ldots$ In a multiplex circuit 5, the signals are successively relayed to a coordinate converter referenced with 6. The coordinate converter 6 contains a respective internal two-dimensional coordinate converter 7 for each rotation. The rotation signals $\alpha$, $\beta$, $\gamma$ are respectively supplied to a sine and cosine converter 8 which relays the corresponding sine or, respectively, cosine signal to the internal coordinate converters. The complete adjustment magnitudes $\Delta x_2$, $\Delta y_2$, $\Delta z_2$ of the jaw-related coordinate system $X_o$, $Y_o$, $Z_o$ are offered at the output of the coordinate converter 6. In the subsequent summing amplifiers 9, these signals are added to the measured coordinates $x_1$, $y_1$, $z_1$ of the measuring point $P_1$. The coordinates of the point $P_2$, $P_3 \ldots P_n$ with respect to the stationary coordinate system X, Y, Z are obtained at the output.

The signal $z_2$ is evaluated for a perspective presentation on a (two-dimensional) monitor 10 by means of a potentiometer 11 with the factor a. As a rule, this factor, given perspective presentation, amounts to 0.5. The output signal from potentiometer 11 is processed with the signals $x_2$, $y_2$ in further summing amplifiers 12 and is supplied to the monitor 10, at which the jaw configuration referenced with 13 is then displayed and its motion can be observed.

For n points ($P_2$, $P_3 \ldots P_n$) to be displayed, 3·n analog memories 4 are to be correspondingly provided which are then sampled by the multiplex means 5 with a specific frequency in the range from one through five kilohertz. The high sampling frequency in this area in comparison to the course of the motion has the advantage that the motion of the points on the monitor 10 can practically ensue simultaneously.

For training purposes, it is advantageous to simulate the measuring point $P_1$ in that the coordinates $x_1$, $y_1$, $z_1$ and $\alpha$, $\beta$, $\gamma$ are replaced by the analog value generators 14 and 15 indicated with broken lines in the presentation according to FIG. 4. With the assistance of this simulation means, the influence of a single measured value of the measuring point $P_1$ on the motion of the other jaw points $P_2$, $P_3 \ldots P_n$ can be observed.

Figure 5:
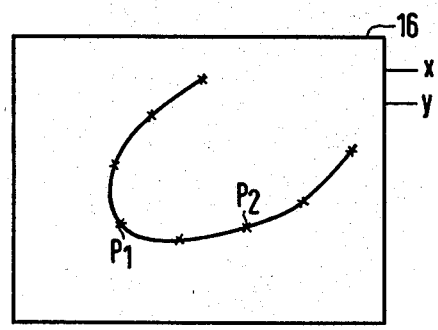
FIGS. 5 and 6 show two possible picture screen displays.

FIG. 5 shows a perspective illustration of the lower jaw model in a two-dimensional plane on a monitor 16 with an X-Y input.

Figure 6:
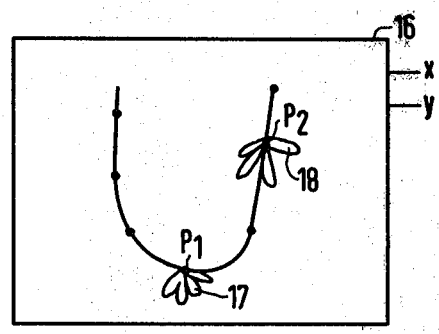

FIG. 6 shows an illustration of the lower jaw model in top view, i.e. in the X-Z plane, and shows a possible course of motion for the points $P_1$ and $P_2$ in a plane perpendicular thereto, for example in the X-Y plane. The chewing patterns (four motion cycles) deriving herefrom for the points $P_1$ and $P_2$ are referenced with 17 or, respectively, 18.

It will be apparent that many modifications and variations may be effected without departing from the scope of the novel concepts and teachings of the present invention.

We claim as our invention:

1. A system for measuring the location, the attitude and/or a change of location or attitude of the lower jaw of a patient, said system comprising a field generator mounted on the lower jaw, field flux sensing means for mounting independently of the field generator and at an interval therefrom and for supplying signals in accordance with field flux from the field generator which define positional information comprising the location and attitude of the field generator relative to said field flux sensing means with respect to a stationary coordinate system (X, Y, Z), an electronic device coupled with said field flux sensing means for obtaining and evaluating the signals from said field flux sensing means, said field generator being located at a measuring point ($P_1$) on the lower jaw such that said electronic device supplies output coordinate signals representing the coordinates ($x_1$, $y_1$, $z_1$) of said measuring point ($P_1$) with respect to the stationary coordinate system (X, Y, Z), and supplies output angular signals ($\alpha$, $\beta$, $\gamma$) representing the angular relationship of the lower jaw with respect to said field flux sensing means, jaw attitude defining means operable for representing the geometrical attitude of the lower jaw relative to said measuring point ($P_1$) and defining a set of joints ($P_2 \ldots P_n$) on the lower jaw with respect to a fixed-body coordinate system ($X_o$, $Y_o$, $Z_o$) assigned to the lower jaw whose origin and center of rotation is said measuring point ($P_1$), and for supplying relative coordinate values ($x_{o2} \ldots x_{on}$, $y_{o2} \ldots y_{on}$, $z_{o2} \ldots z_{on}$) defining the positions of the respective points ($P_2 \ldots P_n$) of said set relative to said measuring point ($P_1$) in said fixed-body coordinate system ($X_o$, $Y_o$, $Z_o$) assigned to the lower jaw, a coordinate converter coupled with said jaw attitude defining means for receiving relative coordinate value signals in accordance with the relative coordinate values ($x_{o2} \ldots x_{on}$, $y_{o2} \ldots y_{on}$, $z_{o2} \ldots z_{on}$) and for converting said relative coordinate value signals related to the lower jaw into adjustment coordinate values ($\Delta x_2 \ldots \Delta x_n$, $\Delta y_2 \ldots \Delta y_n$, $\Delta z_2 \ldots \Delta z_n$) for relating the locations of the respective points of said set to the stationary coordinate system, and summing amplifiers (9) coupled with said electronic device and with said coordinate converter (6) for adding the adjustment coordinate values for the respective points ($P_2 \ldots P_n$) of said set to the output signals of said electronic device representing the coordinates ($x_1$, $y_1$, $z_1$) of said measuring point ($P_1$) with respect to said stationary coordinate system (X, Y, Z).

2. A system according to claim 1 with said jaw attitude defining means comprising a jaw impression model (2) from which the relative coordinate values ($x_{o2} \ldots x_{on}$, $y_{o2} \ldots y_{on}$, $z_{o2} \ldots z_{on}$) of the points ($P_2 \ldots P_n$) are derived.

3. A system according to claim 1, characterized in that, for identifying the geometrical attitude, an x-ray image of the lower jaw (1) is employed from which the relative coordinate values of the points ($P_2 \ldots P_n$) are derived.

4. A system according to claim 3, characterized in that the derivation of the relative coordinate values ensues with the assistance of an opto-electronic scanner.

5. A system according to claim 1, with said jaw attitude defining means comprising analog storage means (4) for storing said relative coordinate values ($y_{o2} \ldots y_{on}$, $z_{o2} \ldots z_{on}$) as analog relative coordinate value signals.

6. A system according to claim 5 with said analog storage means supplying to said coordinate converter said analog relative coordinate value signals, and said electronic device supplying to said coordinate converter angle magnitude signals ($\alpha, \beta, \gamma$) representing the angular relationship of the field generator relative to said field flux sensing means.

7. A system according to claim 6 with said analog storage means comprising a set of three times n analog memories (4), said jaw attitude defining means having a multiplex circuit (5) for coupling of the analog memories (4) with said coordinate converter and operable for supplying to the coordinate converter the analog coordinate value signals for the respective points ($P_2 \ldots P_n$) in sequence.

8. A system according to claim 1 with a monitor (11) having a picture screen for displaying an image comprising said set of points ($P_2 \ldots P_n$) and being coupled with said summing amplifiers (9), and an adjustment means (11) for providing a perspective display on the monitor (10) and operable for supplying a correction factor (a) for taking account of the perspective distortion with respect to the coordinate axis (Z) perpendicular to the surface of the picture screen.

9. A system according to claim 1, with a monitor (11) having a picture screen (16) for displaying an image comprising said measuring point ($P_1$) and said set of points ($P_2 \ldots P_n$), and said points ($P_1 \ldots P_n$) being positioned on the picture screen (16) in one plane while the course of motion of the points is displayed in another plane.

10. A system according to claim 1, further comprising analog value generators (14, 15) for coupling with said summing amplifiers (9) and with said coordinate converter (6) for simulating motion of the measuring point ($P_1$).

11. A system according to claim 1 consisting of only a single field generator.

12. A system according to claim 11, with said single field generator being a magnetic field generator.

* * * * *